United States Patent [19]

Afonso et al.

[11] Patent Number: 5,378,694
[45] Date of Patent: Jan. 3, 1995

[54] ACYL AND ALKOXY SUBSTITUTED QUINOLINES

[75] Inventors: Adriano Afonso, West Caldwell; Jay Weinstein, Upper Montclair; Margaret J. Gentles, Bloomfield; Stuart B. Rosenblum, West Orange, all of N.J.

[73] Assignee: Schering Corporation, Kenilworth, N.J.

[21] Appl. No.: 983,519
[22] PCT Filed: Sep. 6, 1991
[86] PCT No.: PCT/US91/06250
§ 371 Date: Mar. 1, 1993
§ 102(e) Date: Mar. 1, 1993
[87] PCT Pub. No.: WO92/04328
PCT Pub. Date: Mar. 19, 1992

Related U.S. Application Data

[63] Continuation-in-part of Ser. No. 579,749, Sep. 7, 1990, abandoned.

[51] Int. Cl.[6] .................... C07D 215/56; A61K 31/47
[52] U.S. Cl. ........................... 514/82; 514/63; 514/312; 514/432; 514/456; 514/682; 546/14; 546/25; 546/155; 549/23; 549/283; 549/285; 568/328
[58] Field of Search .............. 514/63, 312, 82; 546/14, 25, 155, 156

[56] References Cited

U.S. PATENT DOCUMENTS

| | | | |
|---|---|---|---|
| 3,132,140 | 3/1964 | Daffe | 546/155 |
| 3,960,868 | 6/1976 | Ferrini et al. | 546/156 |
| 4,022,770 | 5/1977 | L'Eplattonio et al. | 546/155 |
| 4,526,894 | 7/1985 | Enomoto et al. | 514/312 |
| 4,738,971 | 4/1988 | Eriksoo | 514/312 |
| 4,959,363 | 9/1990 | Wentland | 514/312 |
| 5,175,151 | 12/1992 | Afonso et al. | 514/63 |
| 5,179,093 | 1/1993 | Afonso et al. | 514/312 |
| 5,179,107 | 1/1993 | Afonso et al. | 514/312 |
| 5,190,956 | 3/1993 | Afonso et al. | 514/312 |
| 5,235,054 | 10/1983 | Jefson | 546/156 |
| 5,268,378 | 12/1993 | Baker | 514/312 |
| 5,310,913 | 6/1994 | Gunnarsson | 546/155 |

FOREIGN PATENT DOCUMENTS

| | | |
|---|---|---|
| 59698 | 9/1982 | European Pat. Off. . |
| 172004 | 2/1986 | European Pat. Off. . |
| 44-16373 | 7/1969 | Japan .................. 546/155 |
| 1207771 | 10/1990 | United Kingdom . |
| 9204328 | 3/1992 | WIPO .................. 546/155 |

OTHER PUBLICATIONS

Derwent Abstract J90005-752-B (1990).
Derwent Abstract J89035-827-B (1989).
Yoshizaki et al. (nom. Abstr vol. 113 Entry 211864z (1990).
Schaefer et al. Chem. Abstr vol. 109 entry 170249z (1988).
Schaefer CA vol. 109 entry 170249Z (1987).
JP 44-16373 (1969).

*Primary Examiner*—Donald G. Daus
*Attorney, Agent, or Firm*—Eric S. Dicker; John J. Maitner; Matthew Boxer

[57] ABSTRACT

Compounds useful as antiviral agents against DNA-containing viruses, such as herpes group viruses, are disclosed. The compounds are are represented by compounds of Formula 1.0:

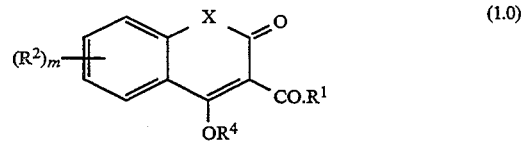

and their pharmaceutically acceptable salts and solvates.

Pharmaceutical compositions containing compounds represented by Formula 1.0 and methods of treating a viral infection using compounds represented by Formula 1.0 are disclosed.

Also disclosed are compounds useful as antihypertensive agents and methods of treating hypertension using such compounds. The antihypertensive agents are compounds represented by Formula 1.0 wherein $R^4$ is selected from the group consisting of alkyl and aminoalkyl. Preferably $R^1$ is H.

14 Claims, No Drawings

ACYL AND ALKOXY SUBSTITUTED QUINOLINES

The present application is the U.S. national application corresponding to International Application No. PCT/US 91/06250, filed Sep. 6, 1991 and designating the United States, which PCT application is in turn a continuation-in-part of U.S. application Ser. No. 07/579,749, filed Sep. 7, 1990, the benefit of which applications are claimed pursuant to the provisions of 35 U.S.C. §§120, 363 and 365(C).

BACKGROUND

EP 595698 discloses heterocyclic carboxamides which increase the activity of the immune system. U.S. Pat. No. 3,960,668 discloses derivatives of 6, 7, or 8 cycloalkyl 4-oxo quinoline 3 carboxylic acid which possess analgesic, anti-inflammatory anti-microbial and histamine liberation inhibiting properties.

This invention relates to compounds having antiviral activity and to compounds having antihypertensive activity, pharmaceutical compositions thereof, and methods of treatment utilizing the compositions. In particular, this invention is related to compounds having antiviral activity against viruses of the herpes group, pharmaceutical compositions containing the compounds, and methods of treating viruses of the herpes group using the pharmaceutical compositions.

There are four separate viruses of the herpes group which infect and cause disease in humans. These are (1) herpes simplex virus 1 and 2 (HSV-1 and HSV-2. respectively): (2) cytomegalovirus (CMV); (3) varicella-zoster virus (VZ); and (4) Epstein-Barr virus (EB). Examples of diseases associated with herpes simplex virus infection include *herpes labialis,* genital herpes *(herpes progenitalis),* neonatal herpes, herpetic keratitis, eczema herpeticum, disseminated herpes, occupational herpes, herpetic gingivostomatitis, meningitis (aseptic), and encephalitis.

CMV is widespread in humans and numerous other mammals. The great majority of human CMV infections are subclinical; that is, the primary infection occurs with no signs or symptoms. An exception to this is a congenital infection which occasionally gives rise to cytomegalic inclusion body disease in infants. There is also a mononucleosis-like syndrome caused by the virus. The great majority of serious cases due to CMV infection come from recurring infections in immuno-compromised patients such as transplant patients and cancer patients. It has been estimated that silent CMV infections have occurred in a majority of humans by the time adulthood is reached.

VZ virus is associated with chicken-pox (varicella) and shingles (zoster) in humans.

EB virus is quite common and causes glandular fever; it is also believed to be responsible for genetic damage that leads to Burkitt's lymphoma.

Examples of drugs used to treat herpes infections include: (1) IUDR (5'-iodo-2'-deoxyuridine); (2) Ara-C (1-[beta-D-arabinofuranosyl]-cytosine); (3) Ara-A (9-[beta-D-arabinofuranosyl]adenine); and (4) Acyclovir (9-[(2-hydroxyethoxy)methyl]guanine). Also Haines et al. (U.S. Pat. No. 4,757,088 issued Jul. 12, 1988) disclose that lidocaine (2-(diethylamino)-N-(2,6-dimethylphenyl)acetamide) is an antiviral agent in cell culture against HSV-1 and HSV-2, and is able to treat herpes virus infections of mammals. Haines et al. also disclose that lidocaine is particularly effective in the treatment of HSV oral and genital lesions in humans. According to Haines et al., the addition of pantothenic acid or its alcohol and salt forms, dexpanthenol and pantothenate respectively, to lidocaine or lidocaine hydrochloride significantly enhances the antiviral activity of those drugs.

Human hypertension is a disease of multiple etiologies. Drugs that act to control one form may not be effective in controlling another. Therefore, further drugs that can be useful in treating hypertension are desirable.

In view of current interest in the an for finding useful antihypertensive agents and useful antiviral agents, in particular, useful agents against viruses of the herpes group, any new compounds exhibiting antihypertensive activity or antiviral activity would be a welcome contribution to the art. This invention provides such a contribution.

SUMMARY OF THE INVENTION

This invention provides compounds which are useful as antiviral agents against DNA-containing viruses such as herpes group viruses. In particular, the compounds of this invention are useful against HSV-1 and HSV-2 and may also prove useful against CMV and EB.

The compounds of this invention are advantageous over known viral compounds because they inhibit early events in viral replication

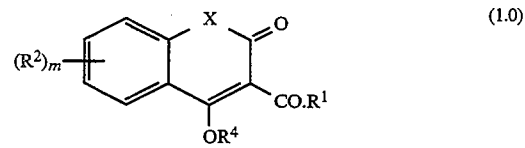

(1.0)

and the pharmaceutically acceptable salts and solvates thereof; wherein:

(A) X is selected from the group consisting of N—$R^3$, O, S, and C($R^3$)$_2$;

(B) $R^3$ is selected from the group consisting of:
  (1) alkyl;
  (2) aralkyl;
  (3) aryl:
  (4) substituted aryl;
  (5) alkaryl;
  (6) alkyl heteroaryl;
  (7) aryloxyalkoxyalkyl;
  (8) —(CH$_2$)$_a$ $R^{11}$ wherein a is an integer of 1 to 6 and $R^{11}$ is selected from the group consisting of —C(O)O$R^{12}$, —O$R^{12}$, —$R^{12}$, and —N($R^{12}$)$_2$, wherein each $R^{12}$ can be the same or different and is selected from the group consisting of alkyl, alkenyl and H; and
  (9) —O$R^{13}$ wherein $R^{13}$ is selected from the group consisting of H, alkyl- which may be substituted with OH, SH, NH$_2$ and/or halogen-, alkaryl, alkenyl, and heteroaryl;

and the two groups $R^3$ on the same carbon atom can be the same or different;

(C) $R^1$ is selected from the group consisting of:
  (1) H;
  (2) alkyl;
  (3) aryl;
  (4) alkaryl;
  (5) alkenyl;

(6) —N($R^5$)$_2$ wherein each $R^5$ is independently selected from the group consisting of H, alkyl- which may be substituted with OH, SH, NH$_2$ and/or halogen-, aryl, alkaryl, alkenyl, heteroaryl, alkoxy, and hydroxy;
(7) heteroaryl; and
(8) substituted alkyl;

(D) Each $R^2$ for each m is independently selected from the group consisting of:
(1) alkyl;
(2) alkoxy;
(3) aryloxy;
(4) aryl;
(5) aralkoxy;
(6) halogen atoms selected from the group consisting of F, Cl, Br and I;
(7) —O—CO—$R^6$ wherein $R^6$ is alkyl- which may be substituted with OH, SH, NH$_2$ and/or halogen-; aryl; alkaryl; alkenyl; and heteroaryl;
(8) —N($R^7$)$_2$ wherein each $R^7$ is independently selected from the group consisting of H, alkyl, aryl, and $R^6$C(O)— wherein $R^6$ is as above defined;
(9) —OH;
(10) —CH$_2$OH;
(11) —COOH;
(12) —COOR$^8$, wherein $R^8$ is selected from the group consisting of alkyl and aryl;
(13) —SO$_3$H;
(14) —SO$_2$NHR$^9$, wherein $R^9$ is selected from the group consisting of alkyl, aryl, and H;
(15) —PO$_3$H;
(16) —PO(OR$^{10}$)$_2$, wherein $R^{10}$ is selected from the group consisting of alkyl and aryl;
(17) —OPO$_3$H;
(18) —OP(OR$^{10}$)$_2$ wherein $R^{10}$ is as above defined; and
(19) —CF$_3$;

(E) m is an integer from 0 to 4; and
(F) $R^4$ is selected from the group consisting of H, aminoalkyl and hydroxyalkyl.

Another embodiment of this invention provides compounds which have antihypertensive activity. The antihypertensive compounds are represented by Formula 1.0 wherein $R^1$, $R^2$, $R^3$, and m are as described above, and $R^4$ is an aminoalkyl group. In these compounds: $R^1$ is preferably hydrogen; $R^4$ is preferably selected from the group consisting of H, —(CH$_2$)$_3$N(CH$_3$)$_2$ and (most preferably) (CH$_2$)$_2$N(CH$_3$)$_2$; $R^2$ is preferably alkyl, more preferably methyl; and most preferably $R^2$ is at the C-6 position.

In still another embodiment this invention provides pharmaceutical compositions useful in treating vital infections or in treating hypertension comprising an effective amount of an antiviral or an antihypertensive compound of this invention together with a pharmaceutically acceptable carrier or excipient. Preferably the antiviral compounds are selected from the group of compounds represented by Formulas 1.3 to 1.25 below. Preferably the antihypertensive compounds are selected from the group consisting of compounds represented by Formulas 1.24 and 1.25 below.

In yet another embodiment this invention provides a method of treating a patient suffering from hypertension or having a viral infection by administering to such a patient an effective amount of an antihypertensive or an antiviral compound of this invention. Generally, in the method of treatment the compound is administered as one of the pharmaceutical compositions of this invention. Examples of viral infections treatable in accordance with the methods of this invention include the DNA-containing viruses such as the herpes viruses discussed above (e.g., HSV-1, HSV-2, CMV, VZ, EB, and the like).

DETAILED DESCRIPTION OF THE INVENTION

When used herein, the terms listed below halve the scope indicated, unless indicated otherwise.

Acyl—represents alkyl-CO-, alkenyl-CO-, alkynyl-CO-, cycloalkyl-CO-, aryl-CO- or-cycloalkenyl-CO-. Preferably acyl represents a compound having the formula —C(O)R$^{14}$ wherein R$^{14}$ is selected from the group consisting of H, alkyl- which may be substituted with OH, SH, NH$_2$ and/or halogen-, aryl, alkaryl, alkenyl, —NH$_2$, —NHR$^{15}$, —N(R$^{15}$)$_2$, heteroaryl, and substituted alkyl, wherein R$^{15}$ is selected from the group consisting of alkyl- which may be substituted with OH, SH, NH$_2$ and/or halogen-, alkaryl, alkenyl and heteroaryl. Representative examples of acyl groups include CH$_3$C(O)—, CH$_3$CH$_2$C(O)—, CH$_3$CH$_2$CH$_2$C(O)—, phenyl-C(O)—, pyridyl-C(O), and the like.

Alkaryl—represents an aryl group, as defined below, in which an alkyl group, as defined below, is substituted for one of the aryl H atoms. The aryl group may contain additional substituents selected from the group consisting of halogen atoms (i.e., Cl, Br, F, and/or I), alkoxy, and amino. Representative examples include CH$_3$phenyl-, CH$_3$CH$_2$phenyl- and the like.

Alkenyl—represents straight and branched carbon chains having at least one carbon-to-carbon double bond and preferably having from 2 to 6 carbon atoms. Preferably the alkenyl substituent has 1 or 2 double bonds. Representative examples include vinyl, allyl, butenyl and the like.

Alkoxy—represents an alkyl radical attached through an oxygen atom (-O-alkyl). Representative examples include methoxy, ethoxy and the like.

Alky—represents straight or branched saturated hydrocarbon chains, which contain from 1 to 6 carbon atoms unless otherwise specified. Representative examples include methyl, ethyl, propyl and the like.

Heteroarylalkyl—represents a heteroaryl group, as defined below, substituting an alkyl group, as defined above. Representative examples include pyridylmethyl, furylmethyl and the like.

Aryloxyalkoxyalkyl—represents a group wherein an aryloxy group substitutes an alkoxy group which in turn substitutes another alkyl group wherein the oxygen atom is attached to the aryl group at a ring carbon atom. Alkoxy is as defined above and aryl is as defined below. The aryl group may contain additional substituents selected from the group consisting of halogen atoms (i.e., Cl, Br, F, and/or ), alkoxy, alkyl, and amino. Representative examples include phenoxypropoxymethyl, phenoxyethoxymethyl and the like.

Aminoalkyl—represents NH$_2$-alkyl-, alkyl-NH-alkyl-, or (alkyl)$_2$N-alkyl- wherein alkyl is as above defined and each alkyl may be the same or different. Representative examples include: aminoethyl, dimethylaminoethyl, dimethylaminopropyl, and the like.

Aralkyl—represents an alkyl group as defined above in which an aryl group as defined below is substituted for one of the alkyl hydrogen atoms. Representative examples include —CH$_2$phenyl, —CH$_2$CH$_2$-phenyl,4-

[(1,1-dimethylethyl)dimethylsiloxy]-phenylmethyl, and the like.

Aralkoxy—represents an aralkyl group as defined above, which is attached through an oxygen atom (aralkyl-O-). Representative examples include phenylmethoxy, phenylethoxy, and the like. The aryl substituent of the aralkyloxy groups contains no other substituents.

Aryl—represents a mono- or bi-cyclic aromatic system. Examples of preferred aryl groups include those having from 6 to 14 carbon atoms. Representative examples include phenyl, 1-naphthyl, 2-naphthyl and indanyl. The aryl group may contain additional substituents selected from the group consisting of halogen atoms (i.e., Cl, Br, F, and/or I), alkoxy, alkyl, and amino.

Aryloxy—represents an aryl group as defined above, which is attached through an oxygen atom (aryl-O-). The aryl group may contain additional substituents selected from the group consisting of halogen atoms (i.e., Cl, Br, F, and/or I), alkoxy, alkyl, and amino. Representative examples include phenoxy, naphthyloxy, and the like.

Cycloalkenyl—represents a carbocyclic ring having from 5 to 7 carbon atoms and at least one carbon-to-carbon double bond in the ring, such as cyclopentenyl, cyclohexenyl, cycloheptenyl, and the like.

Cycloalkyl—represents a saturated carbocyclic ring having from 3 to 7 carbon atoms. Representative examples include cyclopropyl, cyclohexyl, and the like.

Heteroaryl (including the heteroaryl portion of heteroarylmethyl)—represents aromatic systems having at least one O, S and/or N heteroatom in the ring structure. Examples of preferred heteroaryl groups include those containing from 3 to 14 carbon atoms. Representative examples of heteroaryl groups include but are not limited to: 2-, 3- or 4-pyridyl, 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridinyl, 3-, 5- or 6-[1,2,4-triazinyl], 3- or 5-[1,2,4-thiadiazolyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, 2- or 3-pyrrolyl, 2- or 3-N-methylpyrrolyl, and the like.

Hydroxyalkyl—represents an alkyl group, as defined above, wherein one or more hydroxy groups is substituted for one or more hydrogen atoms.

Substituted alkyl—represents an alkyl group, as defined above, wherein one or more of the alkyl H atoms is replaced with groups selected from the group consisting of alkyl, aryl, heteroaryl, —OH, -O-alkyl, —NH$_2$, —N(alkyl)$_2$ wherein each alkyl group may be the same or different, —SH, —S-alkyl, —C(O)O-alkyl, —C(O)H, —NHC(:NH)NH$_2$, —C(O)NH$_2$, —OC(O)NH$_2$, NO$_2$ and —NHC(O)-alkyl, wherein alkyl, aryl, and heteroaryl are as above defined. Examples of substituted alkyl groups include hydroxyethyl, aminoethyl, mercaptoethyl, trifluoromethyl and the like.

Substituted aryl—represents an aryl group, as defined above, wherein one or more of the H atoms attached to the ring carbon atoms is replaced by groups independently selected from the group consisting of halo, alkyl, hydroxy, alkoxy, phenoxy, amino, alkylamino, and dialkylamino. Preferred substituted aryl groups are substituted phenyl groups.

Also as used herein, unless indicated otherwise, C(O) represents C=O, and Ar represents aromatic.

In the compounds of this invention R$^1$ is preferably selected from the group consisting of alkyl, and H. Most preferably R$^1$ is H. Preferably R$^2$ is selected from the group consisting of:
(1) —CH$_3$;
(2) —OCH$_3$;
(3) —OCOCH$_3$;
(4) —OCH$_2$-phenyl;
(5) Cl;
(6) F;
(7) I; and
(8) —CF$_3$.

X is preferably NR$^3$, where R$^3$ is preferably selected from the group consisting of:
(1) —CH$_3$;
(2) —C$_6$H$_{13}$;
(3) —C$_7$H$_5$;
(4) —CH$_2$-phenyl;

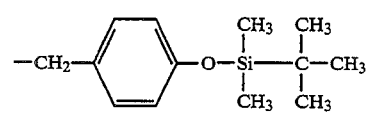

([(1,1-dimethylethyl)dimethylsiloxy]-phenylmethyl);
(6) -phenyl

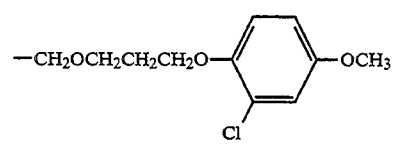

(3-(2-chloro-4-methoxyphenoxy)propoxymethyl);
(8) —CH$_2$CO$_2$CH$_2$CH=CH$_2$; and
(9) —CH$_2$CO$_2$CH$_3$.

Preferably R$^4$ is —(CH$_2$)$_2$N(CH$_3$)$_2$; when R$^4$ is —(CH$_2$)$_2$N(CH$_3$)$_2$, the compounds are preferably used as the maleate or other salt.

A particularly preferred group of compounds of Formula 1.0 includes those wherein:
(A) X is NR$^3$;
(B) R$^1$ is selected from the group consisting of H and alkyl;
(C) R$^2$ is —CH$_3$ and m is 0 or 1;
(D) R$^3$ is selected from the group consisting of:
(1) —C$_6$H$_{13}$;
(2) —C$_7$H$_{15}$; and
(3) —CH$_2$-phenyl; and
(E) R$^4$ is —O(CH$_2$)$_2$N(CH$_3$)$_2$.

Compounds of this invention include compounds selected from the group consisting of the following formulas 1.3 to 1.16, 1.19 and 1.23 to 1.25 (designated below each chemical formula) in the following Table:

TABLE OF CHEMICAL COMPOUNDS

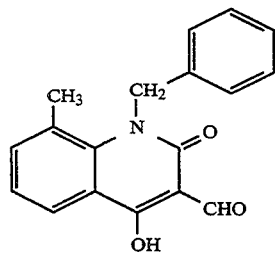

(1.3)

TABLE OF CHEMICAL COMPOUNDS-continued
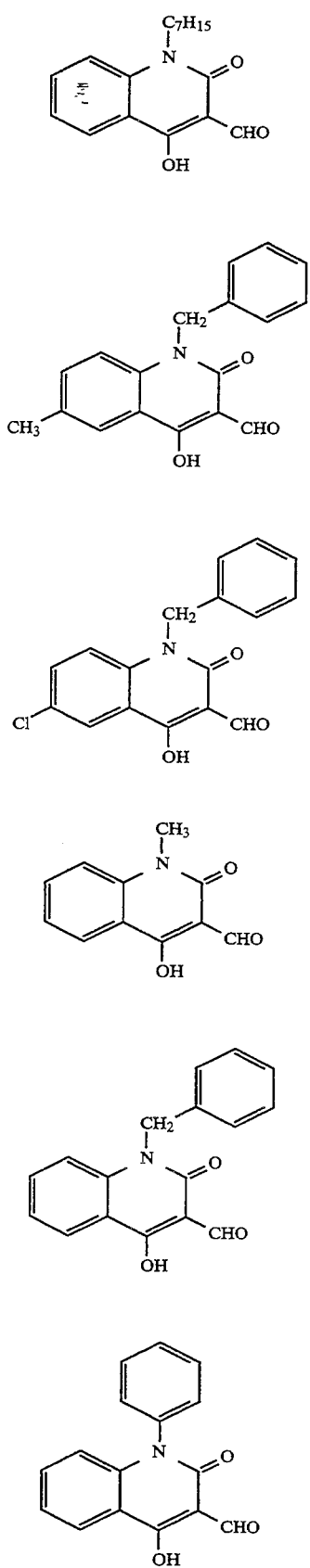
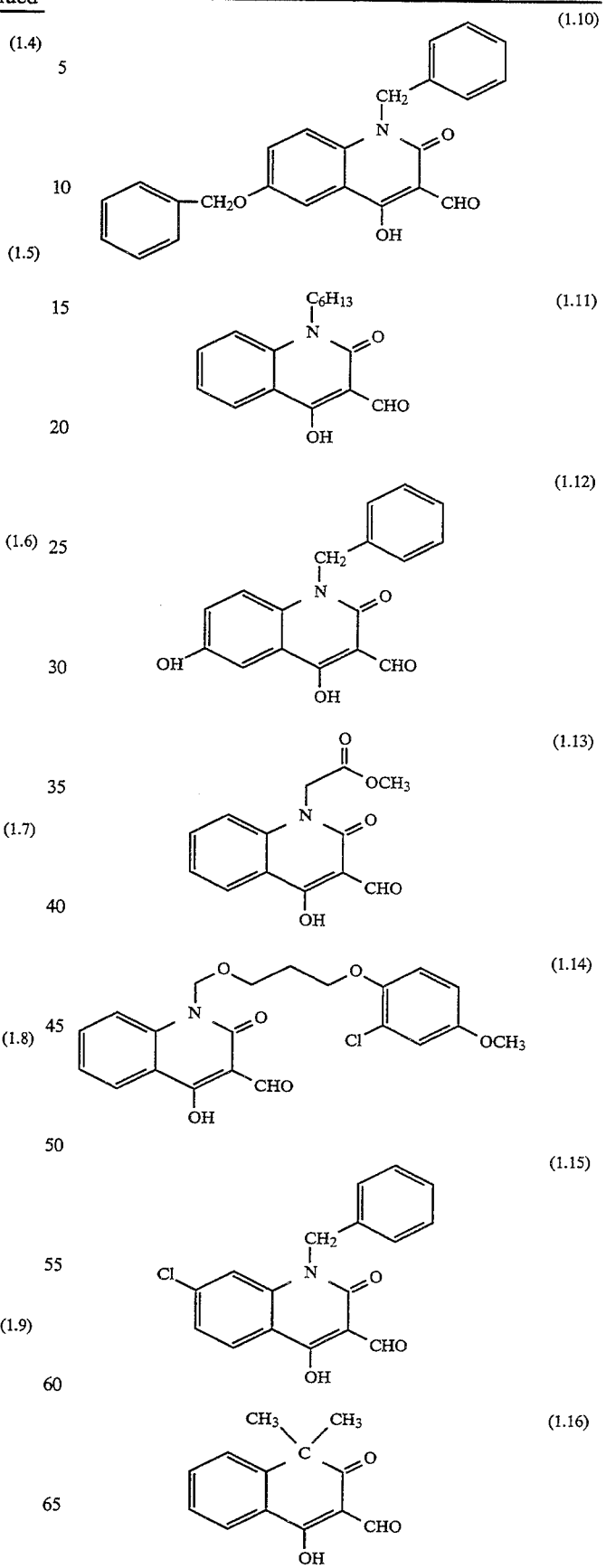

TABLE OF CHEMICAL COMPOUNDS-continued

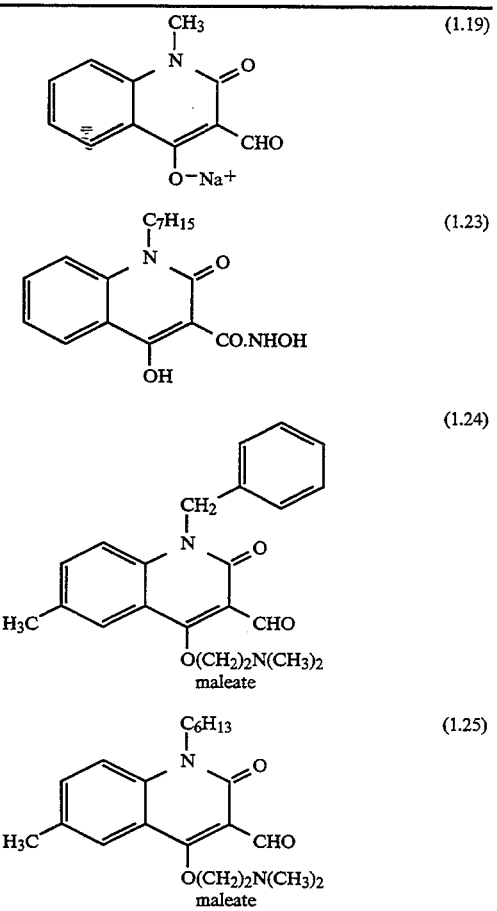

Those skilled in the art will recognize that Formulas 1.24 and 1.25 represent the salts of maleic acid formed at the dimethylamino group of the $-(CH_2)_2N(CH_3)_2$ substitutent.

Certain compounds of this invention may exist in isomeric forms. The invention contemplates all such isomers both in pure form and in admixture, including racemic mixtures.

Certain compounds of the invention can exist in unsolvated as well as solvated forms, including hydrated forms, e.g., hemihydrate. In general, the solvated forms, with pharmaceutically acceptable solvents such as water, ethanol and the like, are equivalent to the unsolvated forms for purposes of the invention.

Certain compounds of the invention will be acidic in nature, e.g., those compounds which possess a carboxyl or phenolic hydroxyl group. These compounds may form pharmaceutically acceptable salts. Examples of such salts are the sodium, potassium, calcium, and aluminum salts. Also contemplated are salts formed with pharmaceutically acceptable amines such as ammonia, alkylamines, hydroxyalkylamines, N-methylglucamine and the like. Preferred salts are the sodium salts of the compounds of Formula 1.0 as exemplified by Formula 1.19. Thus, in the salts of the compounds of this invention, essentially $R^4$ is $M^+$ wherein $M^+$ is one equivalent of one of the metal cations disclosed above.

Certain compounds of the invention, e.g., those with a basic amino group, also form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia or sodium bicarbonate. The free base forms differ from their respective salt forms somewhat in certain physical properties, such as solubility in polar solvents, but the salts are otherwise equivalent to their respective free base forms for purposes of this invention.

The compounds of Formula 1.0 can be prepared by the processes described below. In these processes the substituents are as described above, unless indicated otherwise. Those skilled in the art will appreciate that, in the processes described below, the reactions are carried out at a temperature high enough to allow the reaction to proceed at a reasonable rate, but not so high as to cause undue degradation of reactants and/or products. Those skilled in the art will also appreciate that in the following reactions the desired products may be isolated by techniques well known in the art such as distillation, column chromatography, recrystallization, and the like.

The invention provides a process for the preparation of compounds of Formula 1.0, which comprises one of the following processes (a) to (c):

(a) for the preparation of a compound of Formula 1.0 wherein $R^1$ is a hydrogen atom, the reduction of a corresponding 3-esterified carboxy compound of the formula 2.3:

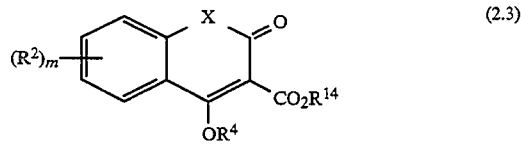

wherein X, $R^2$, $R^4$ and m are as defined for formula 1.0, and $R^{14}$ is an alkyl group, with an appropriate hydride reducing agent;

(b) for the preparation of a compound of Formula 1.0 wherein $R^4$ is hydroxyalkyl or aminoalkyl and $R^1$ has any value defined above for Formula 1.0, the reaction of a compound of Formula B

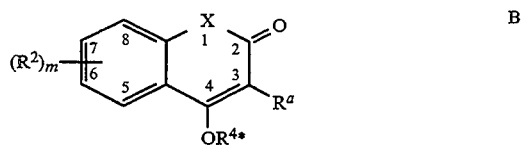

wherein $R^{4*}$ of Formula B is lower alkyl and $R^a$ is CHO, by nucleophilic substitution with $R^4O^-$ in solution in an excess of the alcohol $R^4OH$, wherein $R^4$ is aminoalkyl or hydroxyalkyl;

(c) for the preparation of a compound of Formula 1.0 wherein $R^1$ is an alkyl group, the reaction of a compound of the Formula 2.3 defined in process (a) above, in solution in a suitable solvent, with a metal-alkyl reagent.

In process (a), the compound of the formula 2.3 can be reduced with (for example) one molar equivalent of a reducing agent such as diisobutylaluminum hydride in solution in an inert organic solvent such as an aromatic hydrocarbon solvent (e.g. toluene), preferably at low temperature.

In process (b), the displacement of the radical $OR^{4*}$ (i.e., lower alkoxy, preferably methoxy) at position 4 is preferably effected by means of an excess of the alcohol $R^4OH$, to which a catalytic amount of a strong base such as sodium hydride has been added to generate the anion $R^4O-$. The general reaction can be carried out by following procedures known in the art (see, for example, J. March, *Advanced Organic Chemistry*, cited above, at page 295, the disclosure of which is incorporated herein by reference thereto).

In process (c), the reaction is carried out in a suitable anhydrous solvent such as tetrahydrofuran, preferably with a molar equivalent of an alkylating agent such as a metal alkyl, e.g. a dialkyl-lithiocuprate $(R^1)_2LiCu$.

The starting materials for these processes can be prepared by methods known in the art. For example, a starting material of Formula 2.3 can be prepared by the following sequence of reactions:

In the first step, a suitable 2-substituted benzoic acid 2.0 in aqueous 2N HCl is reacted with trichloromethyl chloroformate to form a compound 2.1, which is an isatoic anhydride when X is NH or $NR^3$. The 2-substituted benzoic acid 2.0 will have the appropriate $R^2$ substituent group(s) to give the desired end product.

When X in the compound of Formula 1.0 is to be $NR^3$, but is NH in the isatoic anhydride of the formula 2.1, then this compound of the Formula 2.1 can be reacted with a suitable $R^3$-halide (wherein $R^3$ is as above defined) to produce the desired $R^3$-substituted isatoic anhydride of the formula 2.1. This is also disclosed by G. M. Coppola et al., *Synthesis*, 505 (1980).

In the second step, the compound of formula 2.1 is reacted with the anion derived from a malonate ester to produce the compound of the formula 2.2 (which is a quinolinone when X is $NR^3$). $R^{14}$ is ethyl when diethyl malonate is used in the reaction.

In the third step, the compound of the formula 2.2 can be reacted with suitable reagents to produce the compound of the formula 2.3 having an ether group at C-4. This reaction can be carried out by standard methods for the preparation of ethers, for example by reaction of an alkali metal salt of the compound of the Formula 2.2

SCHEME I

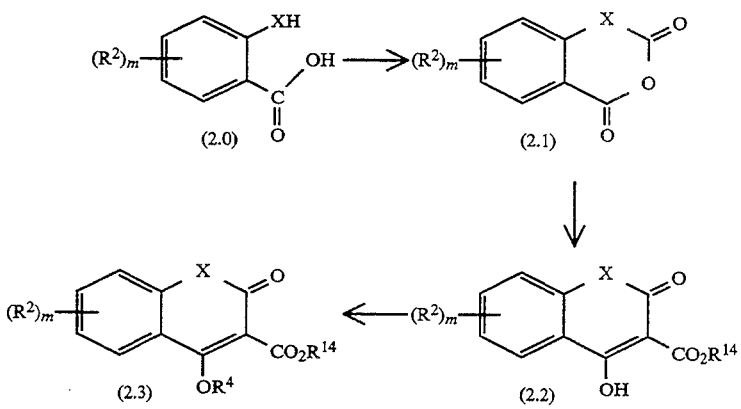

In this Scheme, the radicals X, $R^1$, $R^2$ and $R^{14}$ and m are as defined for Formula 1.0.

The conversion of a compound of Formula 2.0 into a compound of the Formula 2.1, and the conversion of a compound of the Formula 2.1 into a compound of the Formula 2.2, represent reactions well known to those skilled in the art; see for example G. M. Coppola et al., *Synthesis*, 505 (1980), the disclosure of which is incorporated herein by reference thereto.

with a halide $R^4$.Hal (where $R^4$ is preferably alkyl, e.g., $CH_3$), or by reaction of the compound of the Formula 2.2 with a diazoalkane such as diazomethane, in a suitable organic solvent.

A more detailed illustration of the preparation of compounds of the Formula A follows in Scheme II, which shows how the starting materials wherein X is $NR^3$ may be prepared:

SCHEME II

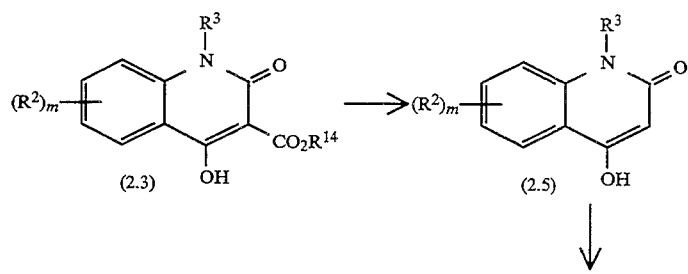

SCHEME II

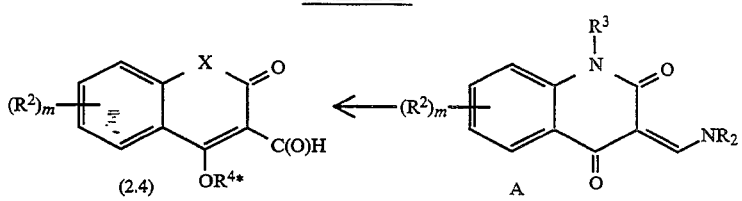

In this Scheme, the radicals $R^2$, $R^3$, $R^4$, and $R^{14}$ and m are as defined for Formula 1.0, and each R is an inert organic group, or the two groups R together with the adjacent nitrogen atom can form a heterocyclic ring containing from 5 to 7 atoms and, if desired, a further heteroatom selected from O, N and S. R is preferably alkyl, especially methyl. The quinolinone 2.3, whose preparation is given in Scheme I above, can be decarboxylated to produce the quinolinone 2.5 by procedures well known in the art, for example by means of alkali; see (for example) G. M. Coppola et al., J. Org. Chem., 41, 825 (1976), the disclosure of which is incorporated herein by reference thereto.

The quinolinone 2.5 can then be convened into the disubstituted aminomethylene quinolinone dione (or enamine) A by reaction with an excess of a dimethylformamide dialkylacetal in an appropriate solvent for a few hours, e.g., with dimethylformamide dimethylacetal in a low-boiling solvent such as dichloromethane.

The enamine of the Formula A can then be hydrolyzed in aqueous solution at acidic pH, e.g. with mineral acid, especially at pH ~3. It usually proceeds to completion in a few minutes at room temperature. $R^{4*}$ in the resulting compound of the Formula 2.4 is hydrogen, and the corresponding compound of the Formula 2.4 wherein $R^{4*}$ is lower alkyl, e.g., methyl, can be prepared by standard methods for the preparation of ethers, for example by reaction of an alkali metal salt of the compound of the Formula 2.4 wherein $R^{4*}$ is a hydrogen atom with a halide $R^{25}$.Hal (where $R^{25}$ is preferably alkyl, e.g., $CH_3$), or by reaction of the compound of the Formula 2.4 with a diazoalkane such as diazomethane, in a suitable organic solvent.

The compounds of this invention can be administered in any number of conventional dosage forms, e.g., topical, oral, parenteral, rectal, transdermal, inhalation and the like. Oral or rectal dosage forms include capsules, tablets, pills, powders, cachets and suppositories. Liquid oral dosage forms include solutions and suspensions. Parenteral preparations include sterile solutions and suspensions. Inhalation administration can be in the form of a nasal or oral spray, or by insufflation. Topical dosage forms can be creams, ointments, lotions, transdermal devices (e.g., of the conventional patch or matrix type) and the like.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, coloring agents, stabilizing agents, emulsifying agents, dispersing agents, suspending agents, pedumes, preservatives lubricants, etc.

Suitable pharmaceutical acceptable solid carriers are magnesium carbonate, magnesium stearate, talc, sugar, lactose, pectin, dextrin, starch, gelatin, tragacanth, methylcellulose, sodium carboxymethylcellulose, low melting waxes, cocoa butter and the like. Capsules can be made wherein the active compound is inserted into pharmaceutically acceptable capsules as a carrier. The active compounds of this invention can be mixed with pharmaceutically acceptable excipients or be used in finely divided powder form without excipients for inclusion into the capsules. Similarly, cachets are included.

Liquid form preparations include solutions, suspensions and emulsions such as water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the active component in finely divided form in water with viscous material, i.e., pharmaceutically acceptable natural or synthetic gums, resins, methylcellulose, sodium carboxymethylcellulose and other well-known suspending agents.

Formulations for topical application may include the above liquid forms, as well as creams, aerosols, sprays, dusts, powders, lotions and ointments which are prepared by combining an active ingredient according to this invention with conventional pharmaceutical acceptable diluents and carriers commonly used in topical dry, liquid, cream and aerosol formulations. Ointment and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oil base and will, in general, also include one or more of pharmaceutically acceptable stabilizing agents, emulsifying agents, dispersing agents, suspending agents, thickening agents, coloring agents, perfumes and the like.

Powders may be formed with the aid of any suitable pharmaceutically acceptable powder base, e.g., talc, lactose, starch, etc. Drops may be formulated with an aqueous base or non-aqueous base also comprising one or more pharmaceutically acceptable dispersing agents, suspending agents, solubilizing agents, etc.

The topical pharmaceutical compositions may also include one or more preservatives or bacteriostatic agents, e.g., chlorocresol, methyl hydroxybenzoate, propyl hydroxybenzoate, benzalkonium chlorides, etc.

The topical pharmaceutical compositions may also contain an active compound of this invention in combination with other active ingredients such as antimicrobial agents, particularly antibiotics, anesthetics, analgesics and antipruritic agents.

Also included are solid form preparations which are intended for conversion, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses under conditions which retard possible decomposition. The solid form preparations intended to be converted to liquid form may contain, in addition to the active material, pharmaceutically acceptable flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of this invention may also be deliverable transdermally for systemic distribution. The transdermal compositions can take the form of creams, lotions and/or emulsions and can be included in a transdermal patch of the matrix or reservoir type as are conventional in the art for this purpose.

The compounds of this invention may be administered by any conventional mode of administration by employing an effective antiviral amount of the appropriate compound of this invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small amounts until the optimum effect under the circumstances is reached. For convenience, the total daily dosage may be divided and administered in portions during the day if desired.

Thus, depending on the mode, dosages of from about 0.1 to about 100 mg/kg of body weight per day may be administered to provide antiviral activity. For example, when administered orally doses of from about 20 to about 60 mg/kg of body weight may be used; and when administered parenterally, e.g., intravenously, dosages of from about 5 to about 20 mg/kg body weight may be used.

When administered topically, the amount of compound administered varies widely with the amount of skin being treated, as well as with the concentration of active ingredient applied to the affected area. Preferably, topical compositions contain from about 0.10 to about 10 percent by weight of the active ingredient and are applied as needed according to the judgment of the attending clinician. When administered rectally, the compounds of this invention may be administered in daily doses ranging from about 0.1 mg/kg to about 100 mg/kg.

The dosage to be administered and the route of administration depends upon the particular compound used, the age and general health of the patient and the severity of the viral condition. Thus, the dose ultimately decided upon must be left to the judgment of a trained health-care practitioner.

EXAMPLES

The following Examples are illustrative only and should not be construed as limiting the invention in any way. Those skilled in the art will appreciate that variations are possible which are within the spirit and scope of the appended claims.

PREPARATION A

Preparation of
1-Benzyl-4-Hydroxy-6-Methyl-2(1H)-Quinolinone

Step (1): Preparation of 6-Methyl-Isatoic Anhydride.

A solution of 2-amino-5-methyl-benzoic acid (4.5 gm) in 2N HCl (15 ml) and water (35 ml) was stirred vigorously while trichloromethyl chloroformate (5.6 gm) was added dropwise. The reaction was stirred for an additional 10 mins and then filtered; the solid cake was washed with water and dried under reduced pressure to give 6-Methyl-Isatoic Anhydride as a light yellow powder (4.7 gm).

Step (2): Preparation of 1-Benzyl-6-Methyl-Isatoic Anhydride.

A solution of 6-methyl-isatoic anhydride (4.5 gm) in DMF (30 ml) was added dropwise to a stirred suspension of 60% sodium hydride (1.0 gm) in DMF (20 ml) under nitrogen atmosphere. The reaction was then warmed to 45° C. and stirred until hydrogen evolution ceased. It was then cooled and a solution of benzyl bromide (4.4 gm) in DMF (10 ml) was added slowly. Stirring was continued for one hour at room temperature and the solution was then evaporated under reduced pressure at 45° C. The resulting solid was suspended in methylene chloride, the insoluble inorganic solid was removed by filtration and the filtrate was evaporated to give 1-benzyl-6-methyl-isatoic anhydride as a crystalline solid.

Step (3): Preparation of 1-Benzyl-3-Ethoxycarbonyl-4-Hydroxy-6-Methyl-2(1H)-Quinolinone.

A solution of diethyl malonate (4.07 gm) in dimethyl acetamide (10 ml) was added dropwise to a stirred suspension of 60% sodium hydride (1.01 gm) in the same solvent (10 ml), under a nitrogen atmoshphere, in an oil bath at 25° C. After hydrogen evolution ceased, the temperature was raised to 80° C. while adding a solution of 1-benzyl-6-methyl-isatoic anhydride (4.5 gm) in DMA (50 ml). After carbon dioxide evolution ceased, the reaction mixture was heated at 120° C. for 17 hours and then was concentrated under reduced pressure to a volume of 25 ml. and then was diluted with water (50 ml). The milky solution was washed with ether, the aqueous layer was acidified with mineral acid to pH3 and the resulting crystalline product 1-benzyl-3-ethoxycarbonyl-6-methyl-2(1H)-quinolinone was isolated by filtration.

Step (4): Preparation of 1-Benzyl-4-Hydroxy-6-Methyl-2(1H)-Quinolinone.

The product from Step (3) was dissolved in 2N sodium hydroxide (150 ml) and the solution was refluxed for 4 hours. Then the solution was cooled and acidified with mineral acid to pH3. The solid was filtered off, dried and crystallized from ethyl acetate/hexane to give 1-benzyl-4-hydroxy-6-methyl-2(1H)-quinolinone (4.0 gm). That the expected product was obtained was confirmed by the spectral data: MS: m/e 265 (M.+); NMR (DMSO): δ2.32 (s, 3H, CH$_3$-Ar), 5.43 (s, 2H, CH$_2$-Ar), 5.96 (s, 1H, =CH—), 11.48 (s, 1H, OH) ppm.

PREPARATION B

Preparation of
1-Methyl-3-Formyl-4-Hydroxy-2(1H)-Quinolinone (Formula 1.7)

Step (1): Preparation of 1-methyl-3-dimethylaminomethylene-(1H)-quinolin-2,4-dione A suspension of 1-methyl-4-hydroxy-2(1H)-quinolinone (1.0 gm) in dimethyl formamide dimethyl acetel (5 ml) and methylene chloride (2.0) was refluxed for 1 hr. The resulting dark orange solution was evaporated under reduced pressure to give 1-methyl-3-dimethylamino-methylene-(1H)-quinolin-2,4-dione.

Step (2): Preparation of 1-methyl-3-formyl-4-hydroxy-2(1H)-quinolinone.

The product from Step (1) was dissolved in distilled water (50 ml) by gentle warming and then the resulting solution was filtered. The clear filtrate was cooled in an ice bath and acidified to pH3 with mineral acid. The resulting crystalline precipitate was washed with water and dried to give 1-methyl-3-formyl-4-hydroxy-2(1H)-quinolinone. That the expected product was obtained was confirmed by the spectral data: MS: m/e 203 (M.+); NMR (CDCl$_3$): δ3.6 (s, 3H, NCH$_3$), 10.28 (s, 1H, CHO) ppm.

EXAMPLES 1 TO 16

EXAMPLE 1

Preparation of
1-Benzyl-4-Formyl-4-Hydroxy-8-Methyl-2(1H)-Quinolinone (Formula 1.3)

Step (1): Preparation of 1-Benzyl-4-Hydroxy-8-Methyl-2(1H)-Quinolinone.

Starting with 2-amino-3-methylbenzoic acid and following the procedure set forth in Preparation A, 1-benzyl-4-hydroxy-8-methyl-2(1H)-quinolinone was produced. That the expected product was obtained was confirmed by the spectral data: m/e 266 (M.+ +1); NMR (DMSO): δ2.46 (s, 3H, CH$_3$-Ar), 5.58 (s, 2H, CH$_2$-Ar), 5.96 (s, 1H, =CH—), 11.5 (br, 1H, OH) ppm.

Step (2): Preparation of 1-Benzyl-3-Formyl-4-Hydroxy-8-Methyl-2(1H)-Quinolinone.

Following the procedure set forth in Preparation B, 1-benzyl-4-hydroxy-8-methyl-2(1H)-quinolinone was converted to 1-benzyl-3-formyl-4-hydroxy-8-methyl-2(1H)-quinolinone. That the expected product was obtained was confirmed by the spectral data: MS: role 293 (M.+); NMR (DMSO): δ2.46 (s, 3H, CH$_3$-Ar), 5.68 (s, 2H, CH$_2$-Ar), 10.12 (s, 1H, CHO) ppm.

EXAMPLE 2

Preparation of
1-Heptyl,3-Formyl-4-Hydroxy-2(1H)-Quinolinone (Formula 1.4)

Step (1): Following the procedure set forth in Preparation A, steps (2–4), isatoic anhydride was convened to 1-heptyl-4-hydroxy-2(1H)-quinolinone.

Step (2): Following the procedure set forth in Preparation B, 1-heptyl-4-hydroxy-2(1H)-quinolinone was converted to 1-heptyl-3-formyl-4-hydroxy-2(1H)-quinolinone. That the expected product was obtained was confirmed by the spectral data: m/e 287 (M.+); NMR (DMSO): δ0.88 (t, 3H, CH$_3$—CH$_2$),4.20 (m, 2H, N—CH$_2$), 10.10 (s, 1H, CHO) ppm.

EXAMPLE 3

Preparation of
1-Benzyl-3-Formyl-4-Hydroxy-6-Methyl-2(1H)-Quinolinone (Formula 1.5)

Following the procedure set forth in Preparation B, 1-benzyl-4-hydroxy-6-methyl-2(1H)-quinolinone (obtained by Preparation A) was converted to 1-benzyl-3-formyl-4-hydroxy-6-methyl-2(1H)-quinolinone. That the expected product was obtained was confirmed by the spectral data: MS: m/e 293 (M.+); NMR (DMSO): δ2.35 (s, 3H, CH$_3$), 5.45 (s, 2H, CH$_2$—Ar), 10.14 ( s, 1H, CHO) ppm.

EXAMPLE 4

Preparation of
1-Benzyl-3-Formyl-4-Hydroxy-6-Chloro-2(1H)-Quinolinone (Formula 1.6)

Step (1): Preparation of 1-Benzyl-4-Hydroxy-6-Chloro-2(1H)-Quinolinone.

Starting with 2-amino-5-chlorobenzoic acid and following the procedure set forth in Preparation A, 1-benzyl-4-hydroxy-6-chloro-2(1 H)-quinolinone was obtained. That the expected product was obtained was confirmed by the spectral data: FAB MS: m/e 286 (M.+ +1); NMR (DMSO): δ5.45 (s, 2H, CH$_2$—Ar), 6.0 (s, 1H, =CH—) ppm.

Step (2): Preparation of 1-Benzyl-3-Formyl-4-Hydroxy-6-Chloro-2(1H)-Quinolinone.

Following the procedure set forth in Preparation B, 1-benzyl-4-hydroxy-6-chloro-2(1H)-quinolinone was convened to 1-benzyl-3-formyl-4-hydroxy-6-chloro-2(1H)-quinolinone. That the expected product was obtained was confirmed by the spectral data: MS: m/e 313 (M.+ +1); NMR (DMSO): δ5.48 (s,2H,CH$_2$—Ar), 10.14 (s, 1H,CHO) ppm.

EXAMPLE 5

Preparation of
1-Benzyl-3-Formyl-4-Hydroxy-2(1H)-Quinolinone (Formula 1.8)

Step (1): Preparation of 1-Benzyl-4-Hydroxy-2(1H)-Quinolinone.

Using isatoic anhydride and following the procedure set forth in Steps (2) to (4) of Preparation A, 1-benzyl-4-hydroxy-2(1H)-quinolinone was obtained, That the expected product was obtained was confirmed by the spectral data: MS: m/e 251 (M.+); NMR (DMSO): δ5.47 (s, 2H, CH₂—Ar), 6.03 (s, 1H, =CH), 11.6 (s, H, OH) ppm.

Step (2): Preparation of 1-Benzyl-3-Formyl-4-Hydroxy-2(1H)-Quinolinone.

Following the Procedure set forth in Preparation B, 1-benzyl-4-hydroxy-2(1H)-quinolinone was converted to 1-benzyl-3-formyl-4-hydroxy-(2(1H)-quinolinone. That the expected product was obtained was confirmed by the spectral data: MS (FAB): m/e 370 (M.+ +1); NMR (DMSO): δ5.50 (s, 2H, CH₂—Ar), 10.18 (s, 1H, CHO) ppm.

EXAMPLE 6

Preparation of
1-Phenyl-3-Formyl-4-Hydroxy-2(1H)-Quinolinone (Formula 1.9)

Step (1): Preparation of 1-Phenyl-4-Hydroxy-2(1H)-Quinolinone.

Starting with N-phenylaminobenzoic acid and following the procedure set forth in Preparation A, 1-phenyl-4-hydroxy-2(1H)-quinolinone was obtained. That the expected product was obtained was confirmed by the spectral data: MS: m/e 237 (M.+); NMR (DMSO): δ5.92 (s, 1H, =CH), 11.60 (s, 1H, OH) ppm.

Step (2): Preparation of 1-Phenyl-3-Formyl-4-Hydroxy-2(1H)-Quinolinone.

Following the procedure set forth in Preparation B, 1-phenyl-4-hydroxy-2(1H)-quinolinone was converted to 1-phenyl-3-formyl-4-hydroxy-(2(1H)-quinolinone. That the expected product was obtained was confirmed by the spectral data: MS: m/e 265 (M.+); NMR (DMSO): δ10.08 (s, 1H, CHO) ppm.

EXAMPLE 7

Preparation of
1-Benzyl-3-Formyl-4-Hydroxy-6-Benzyloxy-2(1H)-Quinolinone (Formula 1.10)

Step (1): Preparation of 1-Benzyl-4-Hydroxy-6-Benzyloxy-(2(1H)-Quinolinone.

Starting with 2-amino-5-benzyloxybenzoic acid and following the procedure set forth in Preparation A, 1-benzyl-4-hydroxy-6-benzyloxy-2(1H)-quinolinone was obtained.

Step (2): Preparation of 1-Benzyl-3-Formyl-4-Hydroxy-6-Benzyloxy-2(1H)-Quinolinone.

Following the procedure of set forth in Preparation B, 1-benzyl-4-hydroxy-6-benzyloxy-2(1H)-quinolinone was convened to 1-benzyl-3-formyl-4-hydroxy-6-benzyloxy-2(1H)-quinolinone. That the expected product was obtained was confirmed by the spectral data: MS: m/e 385 (M.+); NMR (CDCl₃): δ5.10 (s, 2H, OCH₂—Ar), 5.49 (s, 2H, NCH₂—Ar), 10.34 (s, 1H, CHO), 14.78 (s, 1H, OH) ppm.

EXAMPLE 8

Preparation of
1-Hexyl-3-Formyl-4-Hydroxy-2(1H)-Quinoline (Formula 1.11)

Step (1): Preparation of 1-Hexyl-4-Hydroxy-2(1H)-Quinolinone.

Following the procedure set forth in Steps (2) to (4) of Preparation A, isatoic anhydride was reacted with hexyl bromide to give 1-hexyl-4-hydroxy-(2(1H)-quinolinone. That the expected product was obtained was confirmed by the spectral data: MS: role 245 (M.+); NMR (DMSO): δ0.9 (t, 3H, CH₃—CH₂—), 4.06 (t, 2H, N—OH₂), 6.18 (s, 1H, =CH), 11.87 (br, 1H, OH) ppm.

Step (2): Preparation of 1-Hexyl-3-Formyl-4-Hydroxy-2(1H)-Quinolinone.

Following the procedure set forth in Preparation B, 1-hexyl-4-hydroxy-(2(1H)-quinolinone was converted to 1-hexyl-3-formyl-4-hydroxy-2(1H)-quinolinone. That the expected product was obtained was confirmed by the spectral data: MS (FAB): m/e 274 (M.+ +1); NMR (DMSO): δ0.90 (t, 3H, CH₃—CH₂), 4.20 (t, 2H, N—CH₂), 10.11 (s, 1H, OHO) ppm.

EXAMPLE 9

Preparation of
1-Benzyl-3-Formyl-4,6-Dihydroxy-2(1H)-Quinolinone (Formula 1.12)

Step (1): Preparation of 1-Benzyl-4,6-Dihydroxy-2(1H)-Quinolinone.

1-Benzyl-4-hydroxy-6-benzyloxy-2(1H)-quinolinone (Step (1) of Example 7) was subjected to hydrogenolysis using a palladium catalyst and acetic acid as a solvent to produce 1-benzyl-4,6-dihydroxy-2(1H)-quinolinone.

Step (2): Preparation of 1-Benzyl-3-Formyl-4,6-Dihydroxy-2(1H)-Quinolinone.

Following the procedure set forth in Preparation B, 1-benzyl-4,6-dihydroxy-2(1H)-quinolinone was converted to 1-benzyl-3-formyl-4,6-dihydroxy-2( 1H)-quinolinone. That the expected product was obtained was confirmed by the spectral data: MS: m/e 295 (M.+); NMR (DMSO): δ5.45 (s, 2H, NCH₂—Ar), 9.92 (s, 1H, OH), 10.15 (s, 1H, CHO) ppm.

EXAMPLE 10

Preparation of
1-[3-(2-Chloro-4-Methoxyphenoxy)Propyloxymethyl]-3-Formyl-4-Hydroxy-2(1H)-Quinolinone (Formula 1.14)

Step (1): Preparation of 1-[3-(2-Chloro-4-Methoxyphenoxy)-Propyloxymethyl]-4-Hydroxy-2(1H)-Quinolinone.

A solution of 2-chloro-4-methoxyphenol (15.5 gm) in DMF (20 ml) was added to a suspension of 60% sodium hydride (4 gm) in DMF (10 ml). To the resulting solution there was added a solution of 3-chloropropyl benzoate (15.5 gm) in DMF (20 ml). The solution was heated at 80° C. for 20 hrs, then diluted with ethyl acetate, then washed with water then dried and then evaporated. The crude product was dissolved in a 1:1 mixture of methanol/THF (40 ml) to which 10% sodium hydroxide (50 ml) was added. The mixture was refluxed for 3 hrs, then diluted with ethyl acetate, then washed with water and then evaporated. The crude product was purified by chromatography on silica gel using 40% ethyl acetate in hexane as the eluting solvent. The product was then dissolved in dichloroethane (40 ml) containing paraformaldehyde (2.25 gm). The solution was cooled in an ice bath and a stream of HCl gas was bubbled through the solution for 3.5 hrs. The solution was then dried over magnesium sulfate and the solvent was then removed under reduced pressure. Following the procedure set forth in Steps (2) to (4) of Preparation A, the resulting 3-(2-chloro-4-methoxyphenoxy) propyloxymethyl chloride was reacted with isatoic anhydride to give 1-[3-(2-chloro-4-methoxyphenoxy)-propyloxymethyl]-4-hydroxy-2(1H)-quinolinone. That the expected product was obtained was confirmed by the spectral data: MS: m/e 389 (M.+); NMR (DMSO): δ1.9 (t, 2H, CH$_2$), 3.65 (t, 2H, CH$_2$O), 3.70 (s, 3H, OCH$_3$), 3.90 (t, 2H, CH$_2$O), 5.65 (s, 2H, NCH$_2$O), 5.84 (s, 1H, =CH).

Step (2): Preparation of 1-[3-(2-Chloro-4-Methoxyphenoxy)-propoxymethyl]-3-Formyl-4-Hydroxy-2(1H)-Quinolinone.

Following the procedure set forth in Preparation B, 1-[3-(2-chloro-4-methoxyphenoxy)propyloxymethyl]-4-hydroxy-2(1H)-quinolinone was converted to 1[3-(2-chloro-4-methoxy)phenoxy)propyloxymethyl]-3-formyl-4-hydroxy-2(1H)-quinolinone. That the expected product was obtained was confirmed by the spectral data: MS: m/e 417 (M.+); NMR (CDCl$_3$): δ2.01 (q, 2H, CH$_2$), 3.75 (s, 3H, OCH$_3$), 3.85 (q, 4H, CH$_2$—O), 10.21 (s, 1H, CHO).

EXAMPLE 11

Preparation of 1-Benzyl-3-Formyl-4-Hydroxy-7-Chloro-2(1H)-Quinolinone (Formula 1.15)

Step (1): Preparation of 1-Benzyl-4-Hydroxy-7-Chloro-2(1H)-Quinolinone.

Following the procedure set forth in Preparation A, 2-amino-4-chlorobenzoic acid and isatoic anhydride were convened to 1-benzyl-4-hydroxy-7-chloro-2(1H)-quinolinone. That the expected product was obtained was confirmed by the spectral data: MS: m/e 285 (M.+); NMR (DMSO): δ5.36 (s, 2H, CH$_2$—Ar), 5.98 (s, 1H, =CH—), 11.75 (br, 1H, OH) ppm.

Step (2): Preparation of 1-Benzyl-3-Formyl-4-Hydroxy-7-Chloro-2(1H)-Quinolinone.

Following the procedure set forth in Preparation B, 1-benzyl-4-hydroxy-7-chloro-2(1H)-quinolinone was converted to 1-benzyl-3-formyl-4-hydroxy-7-chloro-2(1H)-quinolinone. That the expected product was obtained was confirmed by the spectral data: MS (FAB): m/e 314 (M.+ +1); NMR (DMSO): δ5.5 (s, 2H, CH$_2$—Ar), 10.15 (s, 1H, CHO) ppm.

EXAMPLE 12

Preparation of 1,1-Dimethyl-2,4-Diketo-3-Formyl-1,2,3,4-Tetrahydronaphthalene (Formula 1.16)

Step (1): Preparation of α,α-Dimethyl-Homophthalic Anhydride.

A solution of dimethyl ester of homophthalic acid (7.2 g) in dimethylformamide (40 ml) was stirred at room temperature with 60% sodium hydride (1.38 g) for 10 minutes and then methyl iodide (5 ml) in dimethylformamide (10 ml) was added. The reaction was stirred for 1 hour and worked up by diluting with ice, extracting with ethyl acetate and evaporating to constant weight. The residual oil was remethylated under the same conditions as described and the crude product on distillation gave the α,α-dimethylphthalic acid dimethyl ester (5.9 g) which was stirred in tetrahydrofuran (50 ml) and in sodium hydroxide (50 ml) at 90° C. for 24 hours. The reaction was concentrated and then acidified with mineral acid followed by extraction with ethyl acetate. The extracts were evaporated under reduced pressure and the product was dissolved in acetic anhydride and refluxed for 2 hours. The reaction was then evaporated to dryness and azeotroped with benzene to give the title compounds (3.9 g). That the expected product was obtained was confirmed by the spectral data MS: m/e 190 (M.+); NMR (CDCl$_3$): δ1.62 (s, 6H, CH$_3$), 3.62 (s, 3H, OCH$_3$), 3.85 (s, 3H, OCH$_3$).

Step (2): Preparation of α,α-Dimethyl-2,4-Diketo-1,2,3,4-Tetrahydronaphthalene.

A solution of the product from Step (1) (3.9 g) in tetrahydrofuran (40 ml) was reacted with 3M methyl magnesium bromide (10 ml) at −78° C. for 0.5 hr followed by work up by acidification and extraction with ethyl acetate. The extract was concentrated to a low volume (25 ml) and treated with an excess of a solution of diazomethane in ether for 15 minutes followed by evaporation to give 2-(α-methoxycarbonyl-iso-propyl)-acetophenone as an oil (4.1 g). That the expected product was comfirmed by the spectral data: MS: m/e 220 (M.+); NMR (CDCl$_3$): δ1.50 (s, 6H, CH$_3$), 2.08, 3.80 (s, 6H, OCH$_3$). The latter product was dissolved in dimethylformamide (20 ml) and stirred with 60% sodium hydride (0.5 g) at room temperature for 10 mins and then at 40° C. for 20 mins. Work up by diluting the reaction with ice, and acidification with mineral acid, gave the title compound (2.7 g) as a crystalline solid. That the expected product was obtained was confirmed by the spectral data: MS: m/e 188 (M.+); NMR (DMSO): δ1.42 (s, 6H, CH$_3$), 5.62 (s, 1H, CH=), 11.70 (s, 1H, OH).

Step (3): Preparation of 1,1-Dimethyl-2,4-Diketo-3-Formyl-1,2,3,4-Tetrahydronaphthalene:

The product from step (2) was convened to the title compound by following the procedure described in Preparation B. That the expected product was obtained was confirmed by the spectral data: MS: m/e 216 (M.+); NMR (CDCl$_3$): δ1.55, 1.68 (s, 6H, CH$_3$), 9.92, 10.5 (s, 1H, CHO).

EXAMPLE 13

Preparation of 1-Methyl-3-Formyl-4-Hydroxy-2(1H)-Quinolinone, Sodium Salt (Formula 1.19)

Sodium hydroxide (1N, 27 ml) was added to a stirred suspension of 1-methyl-3-formyl-4-hydroxy-2(1H)-quinolinone (6.2 gm, obtained in accordance with Preparation B) in distilled water (200 ml). The resulting neutral solution was filtered through a Millipore filter (0.45μ) and lyophilyzed to give 1-methyl-3-formyl-4-hydroxy-2( 1H)-quinolinone, sodium salt as an amorphous powder. That the expected product was obtained was confirmed by the spectral data: MS (FAB): m/e 248 (M.+ +23); NMR (D$_2$O): δ9.70 (s, 1H, CHO).

EXAMPLE 14

Preparation of 1-Heptyl-3-Hydroxyaminocarbonyl-4-Hydroxy-2(1H)-Quinolinone (Formula 1.23)

Step (1): Preparation of 1-Heptyl-3-Ethoxycarbonyl-4-Hydroxy-2(1H)-Quinolinone.

Following the procedure set forth in Preparation A, steps (2–3) isatoic anhydride was converted to the title compound.

Step (2): Preparation of 1-Heptyl-3-Hydroxyaminocarbonyl-4-Hydroxy-2(1H)-Quinolinone.

A round-bottomed flask was charged with the product from step (1) (493 mg, 1.49 mmole), sodium methoxide (208 mg, 3.85 mmole), hydroxylamine (278 mg, 4.0 mmole) and methanol (10 mL). The reaction was stirred for 24 hrs and the precipitated product was collected by filtration, washed with water and dried in vacuo to give the title compound (40% yield). That the expected product was obtained was confirmed by the spectral data: M.S. (FAB): m/e 319 (M.+ +H); NMR (DMSO-d6): δ8.25 (1 H, d), 7.85 (1H, dd), 7.7 (1H, d), 7.45 (dd), 4.4 (2H, m, CH$_2$N), 2.95 (br s, exchangeable protons), 1.8 (2H, m), 1.55 (8H, m), 0.95 (3H, t, CH$_3$).

EXAMPLE 15

Preparation of 1-Benzyl-3-Formyl-4-((2-Dimethylamino)ethoxy)-6-Methyl

2(1H)-Quinolinone, Maleate (Formula 1.24)

Step (1): Preparation of 1-Benzyl-3-Formyl-4-Methoxy-6-Methyl-2(1H)-Quinolinone

A solution of 1-benzyl-3-ethoxycarbonyl-4-hydroxy-6-methyl-2(1H)-quinolinone (12.4 g, obtained in step 3 of Preparation A) in dichloromethane (50 ml) and methanol (10 ml) was treated with excess diazomethane in ether for 10 mins and was then evaporated. The crude methylation product upon chromatography on silica gel yielded 1-benzyl-3-ethoxycarbonyl-4-methoxy-6-methyl-2(1H)-quinolinone (11.5 g). The latter product (7.13 g) in dry toluene (80 ml) was cooled to −78° C. and a 1M solution of di-isobutyl aluminum hydride (30 ml) was added dropwise in 10 min. After 2.5 hrs of stirring at −78° C., the reaction mixture was worked up by stirring with aqueous ammonium chloride/1N hydrochloric acid followed by extraction with methylene chloride. The crude reduction product was chromatographed on silica gel and crystallized from ethyl acetate/hexane to give 1-benzyl-3-formyl-4-methoxy-6-methyl-2(1H)-quinolinone as a yellow solid (7.8 g). That the expected product was obtained was confirmed by the spectral data: NMR (CDCl$_3$): δ2.40 (s, 3H, CH$_3$), 4.18 (s, 3H, OCH3), 10.58 (s, 1H, CHO); MS (FAB): m/e 308 (M.+ +1).

Step (2): Preparation of 1-Benzyl-3-Formyl-4-((2-Dimethylamino)ethoxy)-6-Methyl 2(1H)-Quinolinone, Maleate 2-Dimethylaminoethanol (2 ml) was stirred with 60% sodium hydride (20 mg) until a clear solution was obtained. Then the product of Step (1) was added. After stirring for 1 hour, the reaction was diluted with ethyl acetate and washed several times with brine. The organic phase was dried and then evaporated to dryness under reduced pressure. The crude product was purified by chromatography on silica gel and dissolved in a solution of maleic acid (200 mg) in ether (30 ml). The resulting suspension was stirred for 1 hour and filtered to give the title compound as yellow crystals. That the expected product was obtained was confirmed by the spectral data: MS (FAB): m/e 365 (M.+ +1); NMR (CDCl$_3$): δ3.12 (s, 3H, CH$_3$—Ar), 3.81 (t, 2H, CH$_2$—N), 4.65 (t, 2H, CH$_2$O), 5.55 (s, 2H, CH$_2$Ar), 6.30 (s, 2H, CH=), 10.50 (s, 1H, CHO).

EXAMPLE 16

Preparation of 1-Hexyl-3-Formyl-4-(2-Dimethylaminoethoxy)-6-Methyl-2(1H)-Quinolinone, Maleate salt (Formula 1.25)

Step (1): Preparation of 1-Hexyl-3-Formyl-4-Methoxy-6-Methyl-2(1H)-Quinolinone

Using hexyl bromide instead of benzyl bromide and following steps (1–3) in Preparation A, 1-hexyl-3-ethoxycarbonyl-4-hydroxy-2( 1H)-quinolinone was obtained. Then, following the procedure set forth in Example 15, Step (1), the 1-hexyl-3-ethoxycarbonyl-4-hydroxy-2(1H)-quinolinone was converted to the title compound. That the expected product was obtained was confirmed by the spectral data: MS: m/e 301 (M.+); NMR (CDCl$_3$): δ4.15 (s, 3H, OCH$_3$), 10.56 (s, 1H, CHO).

Step (2): Preparation of 1-Hexyl-3-Formyl-4-(2-Dimethylaminoethoxy)-6-Methyl-2(1H)-Quinoline, Maleate salt The title compound was obtained by staring with the product from Step (1) and following the procedure described in Example 15, Step (2). That the expected product was obtained was confirmed by the spectral data: MS (FAB): m/e 359 (M.+ +1); NMR (CDCl$_3$): δ3.10 (s, 6H, (CH$_3$)2N), 3.78 (t, 2H, CH$_2$N), 4.60 (t, 2H, CH$_2$O), 6.30 (s, 2H, CH=), 10.45 (s, 1H, CHO).

Those skilled in the art will appreciate that the compound of Formula 1.13 can be prepared by the procedures described in Preparations A and B.

BIOLOGICAL DATA

Cell and Virus Culture

HeLa and Vero cell cultures were maintained in Eagles Minimal Essential Medium (EMEM) which was supplemented with glutamine, penicillin, streptomycin and 10% fetal calf serum (10% EMEM). Stock cultures of HSV-2 (strain MS available from ATCC VR-540) were grown in and harvested from Vero cells. Viral stocks were titered in Vero cells according to established procedures.

Plasmid Constructions

Plasmid pON$^{ori-}$ 245 contains the promoter of the HSV-1 thymidine kinase (tk) gene located immediately 5′ of the E. coli lac Z gene. In this arrangement, the tk promoter controls transcription from the bacterial gene in transient expression assays. Additionally, an SV40 polyadenylation signal is present at the 3′ end of the lac Z gene to allow for the efficient translation of the mRNA in eucaryotic cells. The expression of beta galactosidase in a transient assay using pON 245$^{ori-}$ is dependent upon superinfection of the transfected cells with HSV. Therefore, a compound which interferes with early steps of HSV replication will also inhibit beta-galactosidase production in transfected cells. For example, see European Patent Application No. 88302149.5 filed Mar. 11, 1988 and published Sep. 14, 1988 as 282,330, the disclosure of which is incorporated herein by reference thereto.

Transient Expression of Beta Galactosidase in Transfected Cells

HeLa cells were seeded into 96 well microtiter plates and allowed to grow to 80% confluency (approximately 35000 cells/well). One half microgram of plasmid pON 245$^{ori-}$ DNA was introduced into the cells of each well by the DEAE Dextran precipitation technique (Grabman and Van der Eb, 1973). Four to six hours later, the cells were rinsed with Hank's Balanced Salt Solution (HBSS), overlaid with 10% EMEM and incubated at 37° C. At 24 hours post-transfection, cells were rinsed, overlaid with 10% EMEM again and re-incubated at 37° C. At 48 hours post-transfection, cells were rinsed and overlaid with either EMEM containing 2% fetal calf serum (2% EMEM), 2% EMEM containing HSV-2 (strain MS, Multiplicity of Infection [moi]=5 pfu/cell) or 2% EMEM containing HSV-2 and the appropriate concentration of the compound to be tested. Twenty-four hours later, the cells were harvested and assayed for beta-galactosidase activity as described below.

Beta Galactosidase Assay

All determinations of beta galactosidase activity were performed in 96-well microtiter plates. The intracellular level of beta-galactosidase activity in each well was determined from cell lysates of the monolayer cultures. Aliquots were assayed by incubation in the presence of beta-galactosidase substrate, 4-methylumbelliferyl-$\beta$-D-galactoside (MUG, 125 ug/ml, Sigma), for 2 hours. The generation of fluorescent product was quantified on a Microfluor microfluorimeter (Dynatech) after addition of 0.1M glycine, pH 10.3 (Spaete and Mocarski, 1985). The inhibitory activity of a compound was plotted versus the concentration and an $IC_{50}$ value (the concentration in mcg/ml of compound required to reduce beta-galactosidase expression by 50%) was obtained for each compound tested.

Compound Toxicity Assay

Compounds which demonstrated a significant inhibitory activity in the HeLa cell beta-galactosidase assay were assayed for their inhibitory effect on HeLa cell translation. HeLa cells were treated with inhibitory compound for 24 hours, after which levels of translational activity were assayed.

For assay of translational activity, HeLa cultures were grown to 80% confluency in 96 well microtiter plates, treated with appropriate concentrations of compound in 2% EMEM during an overnight incubation at 37° C., then rinsed with HBSS and overlaid with 0.8 ml of 2% EMEM containing 8 $\mu$Ci of tritiated leucine ($^3$H-LEU, 141 Cu/mMol, Amersham Corp., Arlington Heights Ill.). After a 1 hour incubation at 36.5° C., the cells were rinsed twice with phosphate-buffered saline (PBS) and lysed in 400 ul/well of 1 × PBS, 0.5% sodium dodecyl sulphate (SDS). After a 10 min incubation at 36.5° C., the contents of the well were transferred to a well in a Millititer HA microfiltration plate (Millipore Corp., Bedford, Mass.). The TCA-insoluble proteins were precipitated onto the filter disc by a 10 min fixation with 5% TCA, followed by filtration under vacuum and three 10 minute rinses with 95% ethanol. The filters were dried at room temperature, cut from the milltitier plate and transferred to scintillation vials. TCA-precipitable counts were assayed in 5 ml of Scintisol (Isolab, Akron, Ohio). The inhibitory activity of a compound was plotted versus the concentration and an $IC_{50}$ value (that concentration of the compound required to decrease cellular translational activity by 50%) was derived for each compound.

Analysis of In Vivo Efficacy

The in vivo assessment of anti-HSV efficacy was determined in the prophylactic guinea pig model of HSV infection described by Stansberry et al. (1982). Dosing of guinea pigs comprised an initial treatment with test compound given 24 hours prior to virus infection and subsequent administration of the compound every eight hours (T.I.D.) for a total of 10 days. Test compounds were administered subcutaneously in 0.5% buffered methyl cellulose at a dose of 60 mg per kg body weight of the animal. Animals were monitered daily for the development of genital lesions and neurological symptomology, both of which were recorded and compared to the results obtained with parallel groups which received placebo or acyclovir. Efficacy was evaluated for each compound by scoring the ability of the compound to ameliorate genital lesions produced by infection with HSV-2, strain MS, expressed as Maximum Lesson Scores (MLS) on a scale of 1 (least lesions) to 4 (severe lessons).

The In vitro Anti-HSV Activity

The in vitro anti-HSV activity is set forth in Table I.

TABLE I

| EX | FORMULA | ANTI-HSV ACTIVITY HSV-$\beta$-Gal ASSAY $IC_{50}$ (mcg/ml) | CYTOTOXICITY $^3$H-LEU ASSAY $IC_{50}$ (mcg/ml) |
|---|---|---|---|
| 1 | 1.3 | 3 | 29 |
| 2 | 1.4 | 4, 4* | 32, 22 |
| 3 | 1.5 | 4 | 16 |
| 4 | 1.6 | 4 | 15 |
| PREP B | 1.7 | 7, 7* | 56, 40 |
| 5 | 1.8 | 7 | 29 |
| 6 | 1.9 | 8 | 12 |
| 7 | 1.10 | 10 | 32 |
| 8 | 1.11 | 8 | 20 |
| 9 | 1.12 | 13 | — |
| 10 | 1.14 | 18 | — |
| 11 | 1.15 | 5 | 23 |
| 12 | 1.16 | 7 | 34 |

*Repeat

In Vivo Anti-HSV Activity
In vivo anti-HSV activity is set forth in Table II.

TABLE II

| Formula | MLS[1] | Neurological Dysfunction (%)[2] |
|---|---|---|
| Placebo | 2.22 | 66 |
| Acyclovir | 1.61 | 44 |
| 1.9 | 0.67 | 0 |

[1]Maximum Lesion Scores on a scale of 1 to 4.
[2]Percentage of animals developing loss of bladder/hindlimb control.

Antihypertensive Activity

I. SHR Assay

The ability of the compounds to lower blood pressure can be assessed in vivo in conscious spontaneously hypertensive rats (SHRs). SHR males are purchased from Taconic Farms, Germantown, N.Y. and are approximately 16-18 weeks old when anesthetized with ether. The caudal (ventral tail) artery is cannulated with polyethylene tubing (PE50), and blood pressure and heart rate are recorded as described by Baum, T. et. al., J. Cardiovasc. Pharmacol., Vol 5, pp. 655-667 (1983). Rats are placed into plastic cylindrical cages where they rapidly recover consciousness. Blood pressure and heart rate are allowed to stabilize for approximately 90 minutes prior to administration of the test compound. Compounds are administered orally as solutions or suspensions in 0.4% aqueous methylcellulose vehicle via a feeding needle. The compound or 0.4% aqueous methylcellulose vehicle is given in a volume of 4 ml/kg to SHRs that been fasted overnight. Activity is expressed as the fall in mean blood pressure (MBP) in millimeters of mercury (mm Hg). Compound-induced changes are compared with the changes in an appropriate placebo group.

The SHR results are given in Table III.

TABLE III

| Formula | Dose, P.O. (mpk) | Fall in MBP (mm Hg)* |
|---|---|---|
| 1.3 | 25 | 7 |
| 1.6 | 25 | 48 |
| 1.5 | 50 | 40 |

*1 mm Hg is multiplied by 0.133 to obtain kPa.

II. Phosphodiesterase inhibition in vitro

Phosphodiesterase enzymes are known to hydrolyze cGMP in smooth muscle. High levels of cGMP are associated with the relaxation of vascular smooth muscle and with a consequent subsequent reduction in blood pressure. Thus, it is believed that by inhibiting these phosphodiesterase enzymes, cGMP levels in muscle will be either maintained or increased with a subsequent reduction in blood pressure.

Compounds are evaluated for inhibition of a phosphodiesterase enzyme which hydrolyzes cyclic guanosine monophosphate (cGMP). The enzyme, cGMP phosphodiesterase (cGMP-PDE), is a homogeneous enzyme obtained from bovine lung and purified by ion-exchange chromatography, get filtration, and sucrose gradient centrifugation. cGMP-PDE is highly selective for cGMP. Bovine aorta homogenates and primary cultures of bovine aortic endothelial and vascular smooth muscle celia contain an enzyme with properties very similar to the lung isozyme.

The enzyme assay is performed using a Biornek Automated Pipetting Station. Compounds are dissolved in distilled water or DMSO and diluted with 10% DMSO. Compounds are tested at several concentrations at log intervals, typically 0.1,1.0,10, and 100 μM final concentration.

Assays contain the following components:
1 μM substrate $^3$H-cGMP
50 mM Tris-HCl, pH 7.5, 5 mM magnesium chloride (MgCl$_2$)
0.5 mg/ml snake venom alkaline phosphatase.

Assays are initiated by addition of enzyme and stopped by addition of 10 mM isobutylmethylxanthine, a general phosphodiesterase inhibitor. Assays are performed for 25 minutes at room temperature to achieve 5-10% hydrolysis or substrate. The negatively charged substrates are then separated from guanosine by binding to an anion-exchange resin (AGI-XS) and centrifugation or filtration, and the product is quantitated by scintillation counting in counts.

% Inhibition=100-[(cpm compound-blank)/(cpm control-blank)X100]

Activity is expressed as the IC$_{50}$ value, i.e., the concentration required to inhibit activity of the enzyme by 50 per cent. The cGMP-PDE IC$_{50}$ results are set forth in Table IV.

TABLE IV

| FORMULA | cGMP-PDE IC$_{50}$(μM) |
|---|---|
| 1.3 | 10 |

TABLE IV-continued

| FORMULA | cGMP-PDE IC$_{50}$(μM) |
|---|---|
| 1.6 | 17 |
| 1.5 | 90 |
| 1.9 | 18 |

A compound within the scope of the antihypertensive compounds of this invention did not show optimum antihypertensive activity when tested using the assays described above. This compound is a compound of Formula 1.0 wherein X is N, R$^1$ is H, R$^3$ is —C$_7$H$_{15}$, n is 1, and R$^4$ is —(CH$_2$)$_2$N(CH$_3$)$_2$. The SHR result for this compound was +7 at 25 mpk (p.o.).

The invention having been thus described, it will be obvious that it may be varied in many ways. Such variations are not to be regarded as a departure from the spirit and scope of the invention and all such modifications are included within the scope of the claims.

We claim:

1. A compound of Formula 1.0:

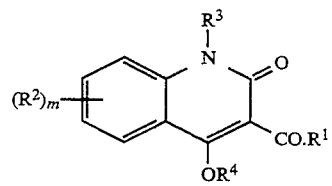

and the pharmaceutically acceptable salts and solvates thereof wherein:

(B) R$^3$ is selected from the group consisting of:
  (1) alkyl;
  (2) —CH$_2$-phenyl;
  (3) phenyl:
  (4) substituted phenyl;
  (7) 3-(2-chloro-4-methoxyphenoxypropyloxymethyl;
  (8) —(CH$_2$)$_a$ R$^{11}$ wherein a is an integer of 1 to 6 and R$^{11}$ is selected from the group consisting of —C(O)OR$^{12}$, —OR$^{12}$, R$^{12}$, and —N(R$^{12}$)$_2$, wherein each R$^{12}$ can be the same or different and is selected from the group consisting of alkyl, alkenyl and H; and
  (9) —OR$^{13}$ wherein R$^{13}$ is selected from the group consisting of H, alkyl- which may be substituted with OH, SH, NH$_2$ and/or halogen -, alkenyl;

(C) R$^1$ is
  (1) H;
  (2) alkyl;
  (5) alkenyl;

(D) Each R$^2$ for each m is independently selected from the group consisting of:
  (1) alkyl;
  (2) alkoxy;
  (3) phenoxy;
  (4) phenyl
  (5) —O—CH$_2$-phenyl;
  (6) halogen atoms selected from the group consisting of F, Cl, Br and I;
  (7) —O—CO—R$^6$ wherein R$^6$ is alkyl- which may be substituted with OH, SH, NH$_2$ and/or halogen -; phenyl; and alkenyl;
  (8) —N(R$^7$)$_2$ wherein each R$^7$ is independently selected from the group consisting of H, alkyl, phenyl, and R⁶C(O)— wherein R⁶ is as above defined;
(9) —OH;
(10) —CH₂OH;
(11) —COOH;
(12) —COOR⁸, wherein R⁸ is selected from the group consisting of alkyl and phenyl;
(13) —SO₃H;
(14) —SO₂NHR⁹, wherein R⁹ is selected from the group consisting of alkyl, phenyl, and H;
(15) —PO₃H;
(16) —PO(OR¹⁰)₂, wherein R¹⁰ is selected from the group consisting of alkyl and phenyl;
(17) —OPO₃H;
(18) —OP(OR¹⁰)₂ wherein R¹⁰ is as above defined; and
(19) —CF₃;
(E) m is an integer from 0 to 1; and
(F) R⁴ is selected from the group consisting of H, aminoalkyl and hydroxyalkyl
and wherein
acyl represents alkyl-C(O)-, alkenyl-C(O)-, alkynyl-C(O)-, cycloalkyl-C(O)-, phenyl-C(O)- or cycloalkenyl-C(O)-;
alkaryl represents an phenyl group, as defined below, in which an alkyl group, as defined below, is substituted for one of the phenyl H atoms;
alkenyl represents straight and branched aliphatic hydrocarbon groups having 1 bond and having from 2 to 6 carbon atoms;
alkoxy represents an alkyl radical attached to a molecule through an oxygen atom (-O-alkyl);
alkyl represents straight or branched saturated hydrocarbon groups which have from 1 to 6 carbon atoms;
aminoalkyl represents NH₂-alkyl, alkyl-NH₂-alkyl, (alkyl)₂NH₂-alkyl;
cycloalkenyl represents a carbocyclic ring having from 5 to 7 carbon atoms and one carbon-to-carbon double bond in the ring;
cycloalkyl represents a saturated carbocyclic ring having from 3 to 7 carbon atoms;
hydroxyalkyl represents an alkyl group wherein one or two hydroxy groups is substituted for one or two hydrogen atoms; and
substituted alkyl represents an alkyl group, as defined above, wherein one of the alkyl H atoms is replaced with a group selected from the group consisting of alkyl, aryl, heteroaryl,—OH, —O-alkyl, —NH₂, —N(alkyl)₂ wherein each alkyl group is the same or different, —SH, —S-alkyl, —C(O)O-alkyl, —C(O)H, —NHC(:NH)NH₂, —C(O)NH₂, —OC(O)NH₂, NO₂ and —NHC(O)-alkyl, wherein alkyl, aryl, and heteroaryl are as above defined;.

2. A compound of claim 1 wherein R² is selected from the group consisting of:
(1) —CH₃;
(2) —OCH₃;
(3) —OCOCH₃;
(4) —OCH₂-phenyl;
(5) Cl;
(6) F;
(7) I; and
(8) —CF₃.

3. A compound of claim 1 wherein R³ is selected from the group consisting of:
(1) —CH₃;
(2) —C₆H₁₃;
(3) —C₇H₁₅;
(4) —CH₂-phenyl;
(6) phenyl;

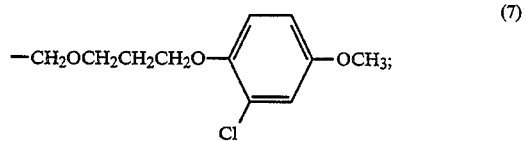

(7)

(8) —CH₂CO₂CH₂CH=CH₂; and
(9) —CH₂CO₂CH₃.

4. A compound of claim 3 wherein:
(A) X is NR³;
(C) R² is selected from the group consisting of:
(1) —CH₃;
(2) —OCH₃;
(3) —OCOCH₃;
(4) —OCH₂-phenyl;
(5) Cl;
(6) F;
(7) I; and
(8) —CF₃; and m is 0, 1 or 2;
(D) R³ is selected from the group consisting of:
(1) —CH₃;
(2) —C₆H₁₃;
(3) —C₇H₁₅;
(4) —CH₂-phenyl;
(6) phenyl;

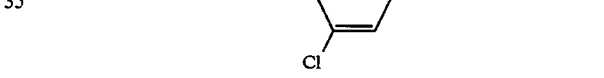

(7)

(8) —CH₂CO₂CH₂CH=CH₂; and
(9) —CH₂CO₂CH₃; and R⁴ is —O(CH₂)₂N(CH₃)₂.

5. The compound of claim 1 wherein R⁴ is an aminoalkyl group.

6. The compound of claim 5 wherein R⁴ is —(CH₂)₂N(CH₃)₂.

7. The compound of claim 6 R² is alkyl.

8. The compound of claim 7 wherein R² is —CH₃.

9. A compound selected from the group consisting of

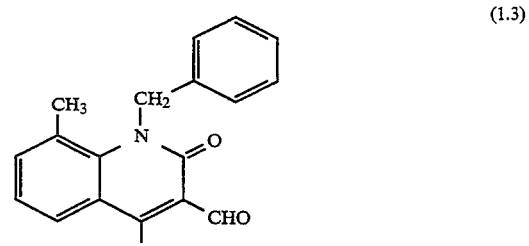

(1.3)

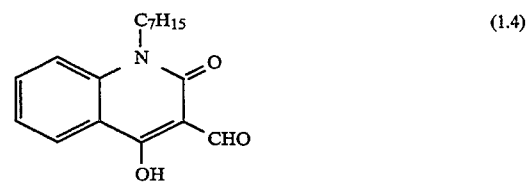

(1.4)

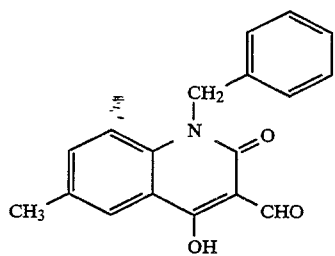 (1.5)
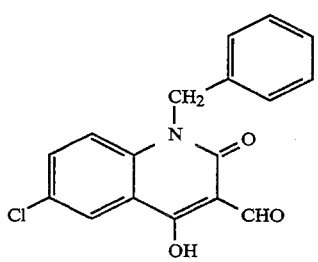 (1.6)
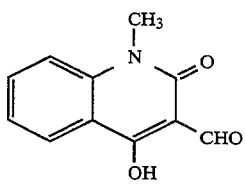 (1.7)
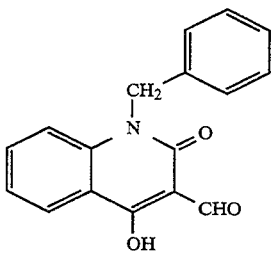 (1.8)
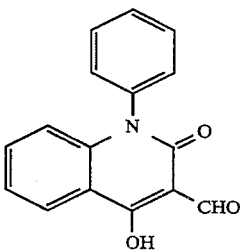 (1.9)
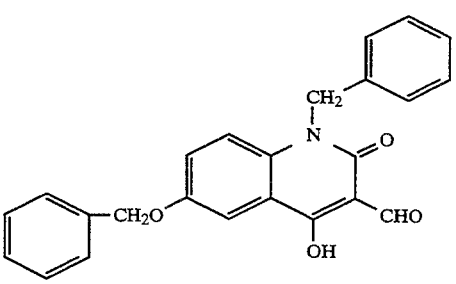 (1.10)
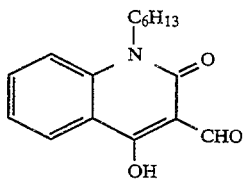 (1.11)
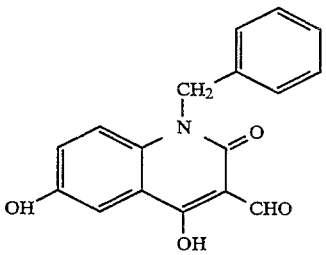 (1.12)
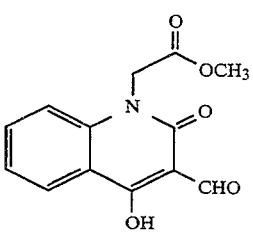 (1.13)
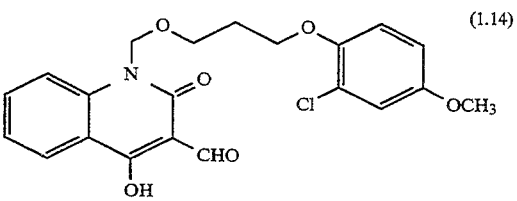 (1.14)
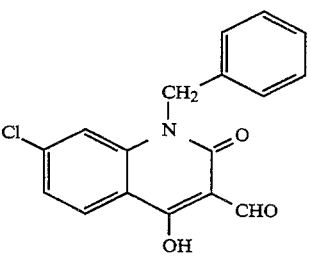 (1.15)
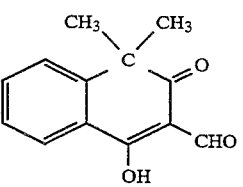 (1.16)
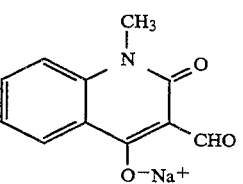 (1.19)

-continued (1.24)

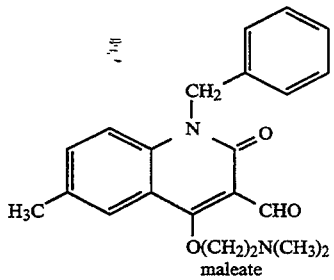

and

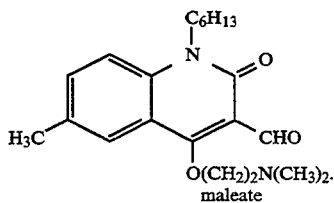

(1.25)

10. A compound selected from the group consisting of (1.24)

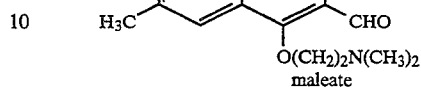

and

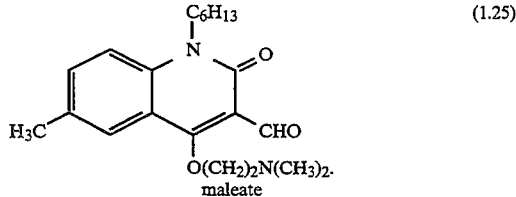

(1.25)

11. The compound of claim 1 wherein:
(B) $R^1$ is selected from the group consisting of H and alkyl;
(C) $R^2$ is —$CH_3$ and m is 0 or 1;
(D) $R^3$ is selected from the group consisting of:
(1) —$C_6H_{13}$;
(2) —$C_7H_{15}$; and
(3) —$CH_2$-phenyl; and
(E) $R^4$ is —$O(CH_2)_2N(CH_3)_2$.

12. The maleate salt of a compound of claim 1 wherein $R^4$ is —$O(CH_2)_2N(CH_3)_2$.

13. A pharmaceutical composition comprising an effective amount of a compound of claim 1 and a pharmaceutically acceptable carrier.

14. A method of treating hypertension in a patient in need of such treatment comprising administering to such patient an effective antihypertensive amount of a compound of claim 5.

* * * * *